United States Patent [19]

Elliott

[11] Patent Number: 4,822,346
[45] Date of Patent: Apr. 18, 1989

[54] CHEST DRAINAGE APPARATUS

[75] Inventor: Donald P. Elliott, Denver, Colo.

[73] Assignee: C. R. Bard, Inc., Murray Hill, N.J.

[21] Appl. No.: 181,189

[22] Filed: Apr. 13, 1988

Related U.S. Application Data

[60] Continuation of Ser. No. 909,779, Sep. 19, 1986, Ser. No. 553,992, Nov. 21, 1983, Ser. No. 341,877, Jan. 22, 1982, Ser. No. 156,920, Jun. 6, 1980, said Ser. No. 341,877, is a division of Ser. No. 156,920.

[51] Int. Cl.$^4$ ............................................. A61M 1/00
[52] U.S. Cl. ..................................... 604/319; 137/205
[58] Field of Search ................. 137/205; 604/317–321, 604/118, 119; 73/861.55

[56] References Cited

U.S. PATENT DOCUMENTS

| | | | |
|---|---|---|---|
| 3,066,530 | 12/1962 | Stenberg | 73/861.55 |
| 3,675,481 | 7/1972 | Phillips | 73/861.55 |
| 3,750,692 | 8/1973 | Tibbs | 604/321 |
| 3,830,238 | 8/1974 | Kurtz et al. | 604/319 |
| 4,015,603 | 4/1977 | Kurtz et al. | 604/318 |
| 4,105,031 | 8/1978 | Kurtz et al. | 604/321 |
| 4,112,948 | 9/1978 | Kurtz et al. | 128/276 |
| 4,261,362 | 4/1981 | Kurtz et al. | 604/321 |
| 4,289,158 | 9/1981 | Nehring | 137/205 |

FOREIGN PATENT DOCUMENTS 2082071 3/1982 United Kingdom ................ 604/319

Primary Examiner—John D. Yasko
Assistant Examiner—J. L. Kruter

[57] ABSTRACT

This invention relates to a novel and improved chest drainage apparatus characterized by a bottle housing a fluid collection chamber and a fluid inlet connectable to receive fluid and air from a chest cavity to be drained, air inlet and exhaust ports downstream of the fluid inlet open to the atmosphere within the air space above the fluid collected, and a U-tube between the fluid inlet and the air exhaust port capable of collecting and retaining an amount of fluid effective to provide a visual indication of any air flow into the system; a subassembly including an air chamber containing a check valve effective when connected to receive air from the exhaust port of the bottle to prevent the backflow thereof into the system; and a negative pressure relief valve connected to the air intake port automatically operative to limit the negative pressure, if any, in the air space above the fluid to a predetermined maximum. The invention also encompasses such an apparatus wherein the subassembly is detachable from the bottle and the latter is used by itself in inverted position as a reservoir of chest fluids that may be reintroduced back into the body. Also included in the apparatus in its preferred form are a positive pressure relief valve downstream of the check valve in the air chamber automatically operative to maintain the air pressure in the latter at or below a predetermined maximum. Additional novel features are those which permit removal of some of the collected fluid either for the purpose of analysis or to extend the capacity thereof.

15 Claims, 2 Drawing Sheets

CHEST DRAINAGE APPARATUS

RELATED APPLICATIONS

This application is a continuation of application Ser. No. 909,779, filed Sept. 19, 1986, application Ser. No. 553,992, filed Nov. 21, 1983, application Ser. No. 156,920, filed June 6, 1980 and application Ser. No. 341,877, filed Jan. 22, 1982, said application Ser. No. 341,877 having been divided from application Ser. No. 156,920.

BACKGROUND OF THE INVENTION

Removing fluids and air from the chest cavity while preventing air from re-entering is an old and well-practiced technique. Under emergency conditions and perhaps at other times where nothing else is available, things like vaseline-coated gauze are used over an open chest wound. Under similar circumstances, one-way flaps made of rubber or plastic have been used for this same purpose along with other contrivances too numerous to mention.

FIELD OF THE INVENTION

Somewhat, but not a great deal, more sophisticated mechanisms are generally used under controlled conditions such as those which exist in the operating room while performing chest surgery. The simplest of these mechanisms is a so-called "water seal" which is nothing more than a bottle to receive the drained fluids and air that is partially filled with sterile water, saline or the drained fluids themselves that has the chest drainage tube from the patient opening beneath the surface of this body of fluid so that the air cannot return by the same route. Such a trap was, and to some extent still is, used with a fluid collection bottle serially connected to the latter but upstream thereof.

The next degree of sophistication added many years ago to the two-bottle chest drainage system described above was a third bottle, again connected serially to the other two, but this time downstream thereof. This third bottle served the function of regulating the vacuum impressed upon the patient's pleural cavity to suck the fluids and air therefrom. It included a tube open to the atmosphere at one end and with the other end opening a preset distance below the level of a supply of fluid contained therein. Functionally, at such time as the negative pressure in the system reached the predetermined level established by the head of fluid above the underwater inlet to the pressure-equalizing tube, it would suck in air from the atmosphere. In this way the patient was protected against negative pressures being impressed upon his or her chest cavity that exceeded a present level. This three-bottle system did not, however, measure the negative pressure to which the patient's chest cavity was subjected. It only placed an upper limit thereon. Thus, with a three-bottle system, the patient is fully protected even if the suction pump fails in the open state or the vacuum line becomes accidently disconnected.

The fourth and final bottle added to the three-bottle system included a vent operative to relieve pressure therein at such time as it rose to a predetermined level. Excessive pressures build-up can occur if, for example, the vacuum pump were to fail in the closed state or the tube leading thereto becomes obstructed and the patient has an active air leak. Under such circumstances, a positive pressure can build up in the patient's pleural cavity leading to what is known as "tension pneumothrax" which can and often does have fatal consequences.

DESCRIPTION OF THE PRIOR ART

The prior art patented chest drainage bottles are, so far as applicant is aware, all owned by Deknatel, Inc. of Queens Village, Long Island, N.Y. Specifically, applicant is aware of their U.S. Pat. Nos. 3,363,627; 3,559,647; and, 3,683,913, all of which relate to some form of multi-compartmented chest drainage apparatus. All three of these patents disclose bottles with a plurality of fluid-filled chambers therein, at least one of which forms the traditional water seal of the prior art two, three and four bottle system while a second defines an underwater safety seal that prevents the build-up of positive presence above a predetermined value.

The aforementioned Deknatel chest drainage bottles are in widespread use today throughout the United States and elsewhere and they perform well to collecting fluids drained from the chest cavity while, at the same time, protecting the latter from excessively high pressures, both positive and negative. These units do, however, have one serious drawback and that is the necessity for printing them before use. In fact, even during use they must be reprimed at intervals because of evaporation which lowers the fluid levels therein and thus changes the pressures at which the "fail-safe" features are designed to function.

SUMMARY OF THE INVENTION

It has now been found in accordance with the teaching of the instant invention that this and other shortcomings of the prior art chest drainage systems can be overcome by the simple, yet unobvious, expedient of eliminating all underwater seals and pressure regulating systems predicated upon fluid head and replacing them with suitable fluidless valve mechanisms that provide accurate pressure regulation, both positive and negative, along with foolproof reverse flow protection. In addition, the instant system not only provides for negative pressure regulation but, in addition, the continuous monitoring thereof. An incidental, but nonetheless important, advantage of the system that needs no priming is the fact that the fluid-filled bottle can be used as a reservoir for returning the fluids collected to the patient's chest cavity, a function that the prior art chest drainage bottles cannot perform. Yet another feature of the instant system which finds no counterpart in the prior art is a transparent fluid-filled U-tube indicator that not only surges back and forth in response to the inhalations and exhalations of the patient but, in addition, provides the observer with a visual indication of any air flowing in the system. Last, but by no means least, is the novel construction wherein all the precision elements of the drainage apparatus are confined to one small detachable subassembly and a poppet-type pressure relief valve thus enabling the fluid collection bottle a relatively imprecise element that can be fabricated by high volume, low cost mass production techniques without adversely affecting the overall precision of the system.

It is, therefore, the principal object of the present invention to provide a novel and improved chest drainage apparatus.

A second objective is the provision of apparatus of the type aforementioned which requires no priming, either initially or during use.

Another object of the within described apparatus is that of providing a low precision fluid collection bottle and a high precision subassembly for use therewith which, along, with a poppet-type pressure relief valve, all cooperate to produce a system possessing, for all practical purposes, the same high degree of precision as its most precise part.

Still another objective is the provision of a chest drainage system wherein the fluid collection bottle that forms an integral part thereof can be used as a reservoir for returning the fluids collected to the chest cavity by merely disconnecting and removing one detachable subassembly therefrom and shutting off the drainage tube.

An additional object is to provide an apparatus of the type herein disclosed and claimed for draining the chest cavity which provides a visual indication of any air flow in the system and, in addition, monitors the negative pressure.

Further objects are to provide a chest drainage apparatus which is safe, relatively inexpensive to manufacture, simpler than the prior art multi-chambered chest drainage bottles, is convenient to use, versatile, compact, lightweight and even decorative.

Other objects will be in part apparent and in part pointed out specifically hereinafter in connection with the description of the drawings that follows.

DESCRIPTION OF THE PREFERRED EMBODIMENT

Figure 1:
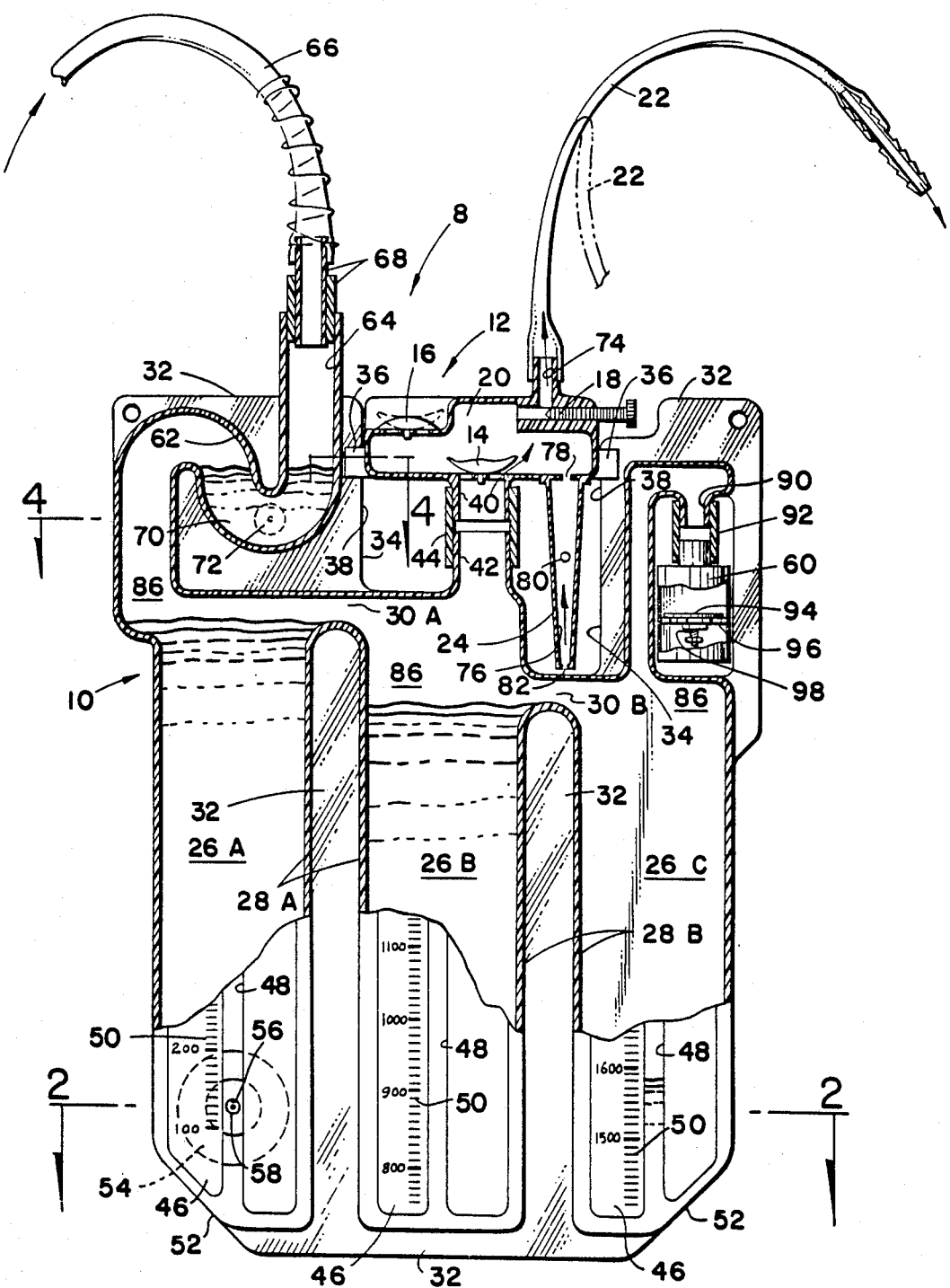
FIG. 1 is a front elevation, portions of which have been broken away and shown in section, revealing the chest drainage apparatus of the present invention in its entirety.

Referring next to the drawings for a detailed description of the present invention and, initially, to FIG. 1 for this purpose, reference numeral 8 broadly designates the chest drainage apparatus in its entirety while numerals 10 and 12 similarly designate the bottle and the control subassembly, respectively. Subassembly 12 is detachably connectable to the bottle and it includes a check valve 14, a positive pressure relief valve 16 and a control valve 18 that regulates the negative pressure in the system. Another element forming a part of subassembly 12 and which will be described in greater detail presently is a negative pressure gauge 24 that also opens onto the interior of air chamber 20.

Figure 2:
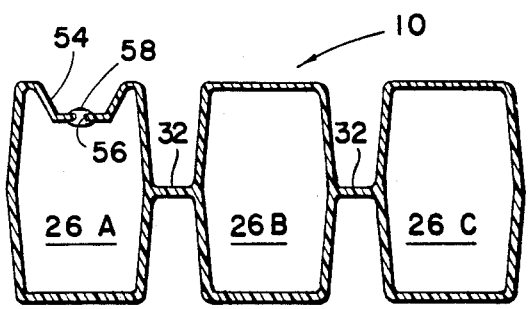
FIG. 2 is a horizontal section therethrough taken along line 2—2 of FIG. 1.

Bottle 10, in the particular form illustrated in FIGS. 1 and 2 will be seen to comprise a unitary blow-molded reservoir defining, among other things, a series of three fluid collection chambers 26A, 26B and 26C separated from one another by partitions 28A and 28B that each contains openings 30A and 30B, respectively, near the top thereof that permit the chest drainage fluids to pass freely from the first to the second when the first is full and from the second to the third when both of the first two are full. These partitions 28 are shown as being double walled and also having an integrally-formed web 32 bridging the gap left between the double walls. This same web extends along the bottom of the bottle and across the top except for the notched-out portion 34 into which subassembly 12 is inserted. Vertically-slotted clips 36 on opposite ends of subassembly 12 slide down the opposed margins 38 of web 32 that border the sides of notch 34 thus detachably-mounting subassembly 12 within the confines of the latter. When thus mounted, tubular air inlet 40 opening into the bottom of air chamber 20 through check valve 14 will be axially aligned with the air outlet 42 in the top of bottle 10. A short hose connection 44 completes the air connection between bottle 10 and the air chamber 20 of subassembly 12.

The bottle is molded from a transparent material that will show the level of the fluid in any of the fluid chambers 26. Each of these three chambers has the front face thereof covered by an adhesive-backed paper label 46 or other suitable scale-carrying member having a vertical slot 48 therein through which the fluid level is visible. The label has printed upon its surface a volumetric scale 50 indicating the total volume of fluid stored at the liquid level visible through slot 48 in the last of the chambers containing fluid. For instance, chamber 26A of the particular bottle illustrate will hold a maximum of 700 cc's of fluid before overflowing into second chamber 26B. This second chamber, in like manner, will hold another 700 cc's even though it can only fill to the level of partition 28B before spilling over into the third chamber 26C. While chamber 26B fills to a level lower than 26A, it holds the same amount due to the truncated corner 52 of the latter. The third chamber 26C is similarly truncated and is designed to fill to the same level as chamber 26B and thus holds less than the other two, specifically, 600 cc's giving a total fluid storage capacity of 2000 cc's. The paper label also provides the nurse with a convenient way of recording thereon the fluid level in the bottle at any observed time.

Figure 5:
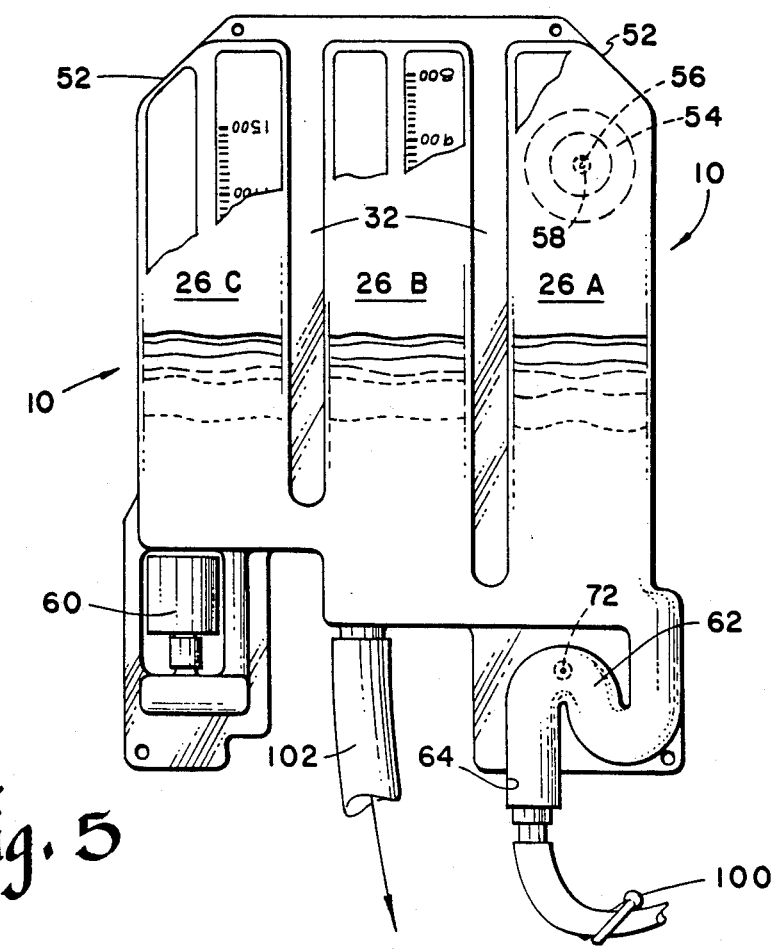

While on the subject of fluid storage capacity, reference should be made to FIGS. 1, 2 and 5, and note should be taken of recess 54 in the back wall of chamber 26A which has an opening 56 at its deepest point sealed by a puncturable grommet 58. If perchance, the bottle is filled to near full capacity, a sterile needle (not shown) can be introduced into chamber 26A through conventional resealable grommet 48 and used to withdraw a considerable quantity of the fluid contained therein thus extending the normal maximum capacity of the bottle. Instances also are encountered occasionally where the capacity of the bottle is too large such as when draining fluid from the chest cavity of an infant or small child. Under such circumstances, it may be desirable to introduce fluid into one or more of the chambers in the form of sterile water or saline. Grommet 58, therefore, can serve either the functions of infusion or withdrawal of fluids from the bottle. The recessed relation of the grommet makes it easier to keep clean and free of contaminants that might otherwise find their way into the bottle when the grommet is entered.

From a functional standpoint, the three serially-connected chambers 26A, B and C are the full equivalent of a single thin chamber three times as deep because both provide precise volume control unattainable with a single shallow chamber of the same capacity. The space-saving advantages of the side-by-side multiple chamber configuration are obvious as are the equally significant gains in terms of simplicity of manufacture. It should be emphasized, however, that these three chambers 26 are used exclusively as reservoirs for the storage of fluid and they have no other function whatsoever; whereas, the prior art multi-compartment bottles each have one or more compartments that must be primed with water which changes their character from that of pure fluid storage vessels to something else. The bottle 10 of the instant chest drainage assembly, therefore, requires little in the way of precision and is thus intended to be disposed of following a single was or repeated use by the same patient. All the precision-made parts of assembly 8 are confined to subassembly 12 with the exception of negative pressure relief valve 60 which is of the conventional poppet-type except that it contains a bacterial filter.

The novel aspects of the bottle 10 are not found in the fluid collection chambers 26, but rather, in such unique features as transparent U-tube 62 formed at the entrance to the fluid collection and storage area defined by compartments 26. The entrance 64 to this U-tube is also the single fluid inlet to the system and it is connected directly to the patient's chest cavity by drainage tube 66. In the particular form shown in FIG. 1, a fluid-tight two-part combination connector and coupling of standard design 68 is interposed between the discharge end of the drainage tube and the inlet 64 to the bottle.

Referring specifically, once again, to FIG. 1, it can be seen that a small volume of fluid 70 will be trapped within the bend in U-tube 62 once fluid begins flowing from the patient. While this U-tube could be primed with a few cc's of sterile water or saline through puncturable grommet 72 disposed near the low point thereof, priming is unnecessary because, in a sense, it is self-priming once fluid begins to flow from the chest cavity. As was the case with grommet 58, grommet 72 can also be used for the purpose of aspirating or otherwise withdrawing a sample of drained fluid to be cultured.

The fluid 70 contained within U-tube 62 is not a water seal effective to prevent the return of air to the patient and, as a matter of fact, the chest drainage assembly of the present invention will perform quite adequately whether there is any fluid in the U-tube or not and irrespective of its level. This is not to say, however, that the fluid filled U-tube has no function. On the contrary, it performs two very significant ones, namely, as both an air leak detector and an indicator of the inhalations and exhalations of the patient as it fluctuates and alternately rises higher in one leg of the U-tube than the other. As the small amount of fluid in the U-tube thus oscillates back and forth under the influence of the differences in pressure caused by the patient's breathing pattern, it provides a clear visual indication that the patient is, in fact, breathing.

The other important functional aspect of U-tube 62 is that of providing a leak detector effective to provide the observer with an instant visual indication of either an air leak in the system or the more serious consequence of an air leak originating in the patient's chest. If, perchance, air bubbles are detected bubbling in a downstream direction through the fluid in the U-tube, the drainage tube 66 should not be either clamped off or removed from the patient until the source of the leak is located. Other than a system leak, the source of air entering bottle 10 comes either from air leaking from the patient's lungs or, alternatively, from aid displaced from the chest cavity by the draining fluid.

The sole function of the so-called water seals in the prior art chest drainage systems is that of preventing the backflow of air into the patient's chest cavity. Such systems must be primed before the water seal becomes operative as previously note. In the instant chest drainage system, on the other hand, no such fluid seal is present because the fluid in U-tube is fully capable of passing air in either direction, i.e. back into the patient as well as out. Instead, a high precision flapper-type check valve 16 located at the interface between fluid collection chambers 76 and the air chamber 20 of subassembly 12 answers this need. Valve 16 responds to an opening pressure of approximately 0.5 cm H$_2$O in the particular embodiment illustrated and it functions completely independently of any fluid present in either the fluid collection chambers or the U-tube.

The full line position of FIG. 1 is the normal operating condition of the system, assuming some air is being evacuated from the patient's chest cavity. Fluids, mostly blood, enter the system through drainage tube 66 when they are collected in chambers 26 after having passed through the U-tube. The air, in turn, while passing through the fluid in the U-tube, bypasses any fluid collected in the fluid collection chambers and, instead, exits the latter through check valve 14 directly into air chamber 20. Under normal operating conditions, a negative pressure environment will exist in chamber 20 due to the vacuum being drawn therein by vacuum line 22 or, alternatively, this line may be left open to the atmosphere for gravity operation. Positive pressure relief valve 16 in the top of chamber 20 will normally remain closed. When maintaining a sub-atmospheric pressure in chamber 20, the fluids and air are aspirated from the patient without he or she having to exert the positive pressure required to force them out.

Vacuum line 22 is connected directly into a vacuum source supplied by the institution. Since such systems provide negative pressures of a magnitude well in excess of that required for chest drainage purposes, the outlet 74 thereto leading out of air chamber 20 is provided with a screw-type pressure regulator 18 operative to control the pressure within the latter and thus the opening pressure of check valve 16 within carefully controlled rather narrow limits.

Now, in the rare event that a malfunction occurs of the type that would result in a positive pressure build-up in air chamber 20, such a happenstance having been indicated by the kinking of the vacuum line 22 shown in phantom lines in FIG. 1, the remote possibility arises that such a positive pressure could blow out check valve 16 thus releasing this pressure back into the chest cavity of the patient with the attendant serious consequences. To prevent this from every happening, positive pressure relief valve 14 is provided in subassembly 12 for the purpose of venting any positive pressure above a predetermined value to the atmosphere before it can re-enter the system. Valve 14 like valve 16 is of the flapper type and set to open at a pressure well below that where valve 14 would be over-ridden and allow air back into the system. The phantom line positions of valves 14 and 16 represent the abnormal positive pressure relief condition just described. It should, perhaps, be noted that the open positions of both these valves have been highly exaggerated in FIG. 2 for purposes of illustration since they actually have to only unseat a tiny fraction of an inch to accomplish their intended functions.

Figure 3:
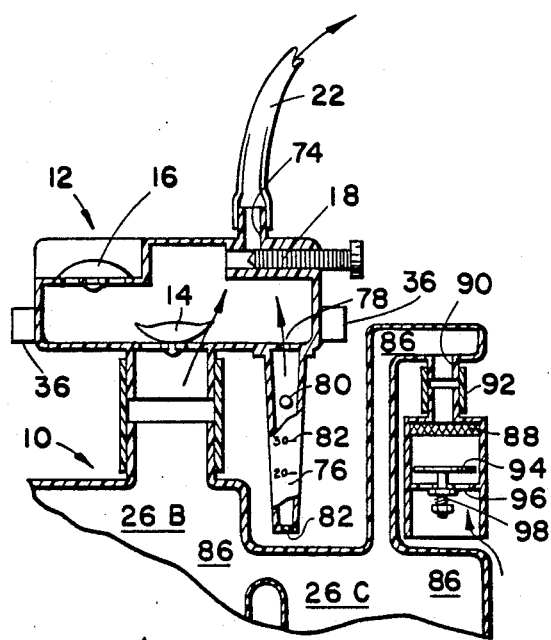
FIG. 3 is a fragmentary section to the same scale as FIG. 1 showing the high negative pressure relief system of the apparatus in operation.
Figure 4:
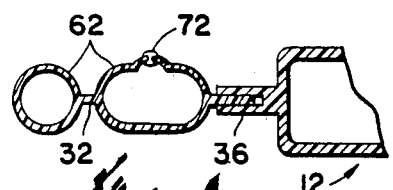
FIG. 4 is a fragmentary vertically offset section taken along line 4—4 of FIG. 1 and to the same scale as the latter; and, FIG. 5 is an elevational view, portions of which have been broken away and shown in section, to a slightly smaller scale than FIG. 1.

One of the most significant and unique features of the chest drainage system forming the subject matter hereof is the negative pressure indicator identified by reference numeral 24 and which forms an integral and functional part of subassembly 20 and which has been shown most clearly in FIGS. 1 and 3 to which detailed reference will now be made. A vertically-disposed upwardly-flaring frustoconical tube 76 opens into the bottom of the air chamber 20 through restricted opening 78 therein, such opening being too small to pass ball 80. A second opening 82 is provided in the small truncated end of tube 76 which, likewise, is sized smaller than ball 80. Opening 82 defines a controlled orifice open to the atmosphere into which air is aspirated at a velocity sufficient to lift ball 80 depending upon the magnitude of the negative pressure gradient thereacross. The outside of tube 76 is provided with scale-forming indicia 84 reading directly in negative pressure measured in cm $H_2O$ or some other suitable set of values.

Now, while floating ball-type indicators of the same general type as that just described have been used for many years to indicate flow rates in a flowing fluid, to applicant's knowledge no such indicator has been used heretofore to read negative pressures existent in the air chamber of a chest drainage system. When so used, the attending physician and others responsible for the safety and well being of the patient are provided with an easily readable pressure gauge constantly monitoring the negative pressure within chambr 20. Having thus described the fail-safe system that becomes functional whenever a positive pressure above a predetermined level is present in air chamber 20, a similar system will next be set forth which responds in like manner to handle abnormal negative pressures within the system for which purpose detailed reference will be made to FIG. 3.

Excess negative pressure are rare but could, conceivably, result from a so-called "milking" or stripping of chest drainage tube 66. If this should occur or if for some reason an abnormal negative pressure is present in air chamber 20, such a condition will immediately exist in the fluid collection chambers 26 as well. If the negative pressure condition occurs upstream of the system, the fluid in U-tube 62 would be sucked out into the discharge tube and ultimately back into the patient's chest cavity if it were not for the presence of negative pressure relief valve 60. Likewise, if a sudden high negative pressure were to occur in air chamber 20 for some reason, relief valve 16 will be closed and check valve 14 will be open exposing the fluid collection chambers 26 and everything upstream thereof including the patient to this abnormal condition. With the instant system, relief valve 60 connected into the fluid free air space 86 above the fluid contained within the fluid collection chambers 26 will respond by opening as illustrated to admit air from the atmosphere thus limiting the maximum negative pressure that can exist in the system to a predetermined level well below that where any backflow to the patient can take place. Negative pressure relief valve 60 is of the more or less common poppet-type except that it incorporates bacterial filter 88 (FIG. 3) which filters the incoming air to prevent contamination of the fluids stored in the fluid collection chambers. Valve 60 is detachably connected to neck 90 of the bottle by means of a short length of hose 92 in the particular form shown. The particular system illustrated has valve 60 set to open at a maximum negative pressure of $-50$ cm $H_2O$ which has proven entirely adequate to protect the patient. Once again, the accuracy necessary for precise controlled operation of the system is found in valve 60 and is not demanded of throw away bottle 10 which merely provides a connection 90 open to the atmosphere upon which to attach same. FIG. 3 illustrates diagrammatically the condition described above where an excessive negative pressure is sensed in air chamber 20 that causes the valve element 94 of valve 60 to move off its apertured seat 96 in opposition to the bias of spring 98 and thus open to maintain the system pressure at a maximum of $-50$ cm $H_2O$.

In closing, reference will be made to FIG. 5 wherein a unique capability of the instant bottle 10 has been illustrated, namely, the use thereof in inverted position as a reservoir to return the previously drained chest fluids back into the patient's chest cavity. Without having to transfer these fluids or otherwise handle them with the attendant risk of contamination, drainage hose 66 is clamped off by clamp 100, subassembly 12 removed and a fluid delivery tube 102 fitted in its place to air outlet 42. Valve 60 need not be removed since it will remain in its normally-closed condition. After tube 102 has been inserted into the patient's chest cavity, the bottle can be inverted to dispense the fluids stored therein by gravity flow. No other chest drainage system to applicant's knowledge has a bottle that can be used in this way.

What is claimed is:

1. A non-waterseal thoracic drainage apparatus comprising:
    means defining a fluid collection chamber having an air space at its upper end;
    an inlet tube in communication with the fluid collection chamber, the inlet tube being connectable to receive fluids and air from a patient's a chest cavity.
    one-way waterless valve means associated with the fluid collection chamber and being operative, unaided by underwater seals, to permit air to flow out of the air space while preventing reverse flow back into the collection chamber;
    means defining a flow path between the inlet tube and said one-way waterless valve means;
    air leak indicator means along said flow path for entrapping a volume of liquid through which air may bubble;
    said air leak indicator means being constructed to provide a visual indication of air passing therethrough; and
    said one-way waterless valve means being openable in response to a low pressure differential.

2. A thoracic drainage apparatus as defined in claim 1 wherein said entrapping means comprises a portion of the flow path being U-shaped.

3. A thoracic drainage apparatus as defined in claim 2 further comprising:
    an outlet port in communication with the air space, the outlet port being adapted to be connected to a source of suction.

4. A thoracic drainage apparatus as defined in claim 3 further comprising:
    suction control means for controlling the level of suction applied to the air space.

5. A thoracic drainage apparatus as defined in any of claims 1–4 further comprising:
    means defining a high negative pressure relief valve in communication with the air space, said relief valve being operative to open whenever the negative pressure in the air space exceeds a predetermined value, the high negative pressure relief valve means being in communication with a source of increased pressure to admit air to the air space when said high negative pressure relief valve means opens.

6. A thoracic drainage apparatus as defined in any of claims 1-5 further comprising:
   positive pressure relief valve means in communication with the air space.

7. A non-waterseal thoracic drainage apparatus comprising:
   means defining a fluid collection chamber having an air space at its upper end;
   an inlet tube in communication with the fluid collection chamber, the inlet tube being connectable to receive fluids and air from a patient a chest cavity;
   one-way waterless valve means associated with the fluid collection chamber and being operative, unaided by underwater seals, to permit air to flow out of the air space while preventing reverse flow back into the collection chamber, said one-way waterless valve means comprising the primary means for preventing said reverse flow;
   means defining a flow path between the inlet tube and said one-way waterless valve means;
   air leak indicator means along said flow path for entrapping a volume of liquid through which air may bubble; and
   said air leak indicator means being constructed to provide a visual indication of air passing therethrough 8. A thoracic drainage apparatus as defined in claim 7 wherein said entrapping means comprises a portion of the flow path being U-shaped.

9. A thoracic drainage apparatus as defined in claim 8 further comprising:
   an outlet port in communication with the air space, the outlet port being adapted to be connected to a source of suction.

10. A thoracic drainage apparatus as defined in claim 9 further comprising:
    suction control means for controlling the level of suction applied to the air space.

11. A thoracic drainage apparatus as defined in any of claims 7-10 further comprising:
    means defining a high negative pressure relief valve in communication with the air space, said relief valve being operative to open whenever the negative pressure in the air space exceeds a predetermined value, the high negative pressure relief valve means being in communication with a source of increased pressure to admit air to the air space when said high negative pressure relief valve means opens.

12. A thoracic drainage apparatus as defined in any of claims 7-11 further comprising:
    positive pressure relief valve means in communication with the air space.

13. A thoracic drainage apparatus as defined in claim 12 further comprising:
    said one-way valve having an outlet side which communicates with the outlet port;
    the positive pressure relief valve having an outlet side which does not communicate with the outlet port thereby to define separate outlet paths for the one-way valve and positive pressure relief means.

14. A thoracic drainage apparatus as defined in any of claims 7-13 wherein the one-way waterless valve means is openable in response to a low pressure differential.

15. A thoracic drainage apparatus as defined in claim 14 wherein said low pressure differential is approximately 0.5 cm water.

* * * * *

Disclaimer 4,822,346—Donald P. Elliott, Denver, Colo. CHEST DRAINAGE APPARATUS. Patent dated April 18, 1989. Disclaimer filed November 14, 2000, by the assignee Genzyme Corporation.

The term of this patent shall not extend beyond the expiration date of Pat. No. 4,747,844.
*(Official Gazette, May 1, 2001)*